United States Patent
Traube et al.

(10) Patent No.: US 8,759,113 B2
(45) Date of Patent: Jun. 24, 2014

(54) DEVICE FOR RECEIVING A LIQUID AND ALSO DEVICE FOR APPLYING LIQUIDS ON SAMPLE CARRIERS AND METHOD FOR THIS PURPOSE

(75) Inventors: Andreas Traube, Nürtingen (DE); Tobias Brode, Esslingen (DE)

(73) Assignee: Fraunhofer-Gesellschaft zur Förderung der angewandten Forschung e.V., München (DE)

( * ) Notice: Subject to any disclaimer, the term of this patent is extended or adjusted under 35 U.S.C. 154(b) by 430 days.

(21) Appl. No.: 12/579,683

(22) Filed: Oct. 15, 2009

(65) Prior Publication Data
US 2010/0112718 A1    May 6, 2010

Related U.S. Application Data

(60) Provisional application No. 61/110,027, filed on Oct. 31, 2008.

(51) Int. Cl.
*G01N 1/00* (2006.01)
*B01L 3/00* (2006.01)

(52) U.S. Cl.
USPC ............ 436/180; 422/522; 422/521; 422/501

(58) Field of Classification Search
USPC ......... 422/501, 509, 515, 516, 517, 518, 521, 422/522; 73/864.01; 222/580, 581, 582, 222/160, 162, 163; 436/180
See application file for complete search history.

(56) References Cited

U.S. PATENT DOCUMENTS

| | | | |
|---|---|---|---|
| 6,841,130 B2 * | 1/2005 | Lehtinen et al. | 422/525 |
| 2001/0005489 A1 * | 6/2001 | Roach et al. | 422/99 |
| 2005/0118074 A1 * | 6/2005 | Hubbard et al. | 422/100 |
| 2007/0077646 A1 * | 4/2007 | Okamoto | 435/288.4 |
| 2007/0258863 A1 * | 11/2007 | Nishimura et al. | 422/102 |

OTHER PUBLICATIONS

Steger, R. et al. "A Highly Parallel Nanoliter Dispensing System Fabricated by High-Speed Micromilling of Polymers." Actuator 2004, from the Proceeding of the 9th International Conference on New Actuators, exhibited Jun. 14-16, 2004. Paper p. 38. pp. 545-548.*

Steger, Reinhard et al. "The dispensing well plate: A novel device for nanoliter liquid handling in ultra high-throughput screening." Journal of the Association of Laboratory Automation (2004) 9 291-299.*

\* cited by examiner

*Primary Examiner* — Christopher A Hixson
(74) *Attorney, Agent, or Firm* — Matthew B. Dernier, Esq.; Gibson & Dernier LLP

(57) ABSTRACT

Methods and apparatus providing for receiving liquids and for applying liquids on sample carriers.

13 Claims, 2 Drawing Sheets

Figur 1
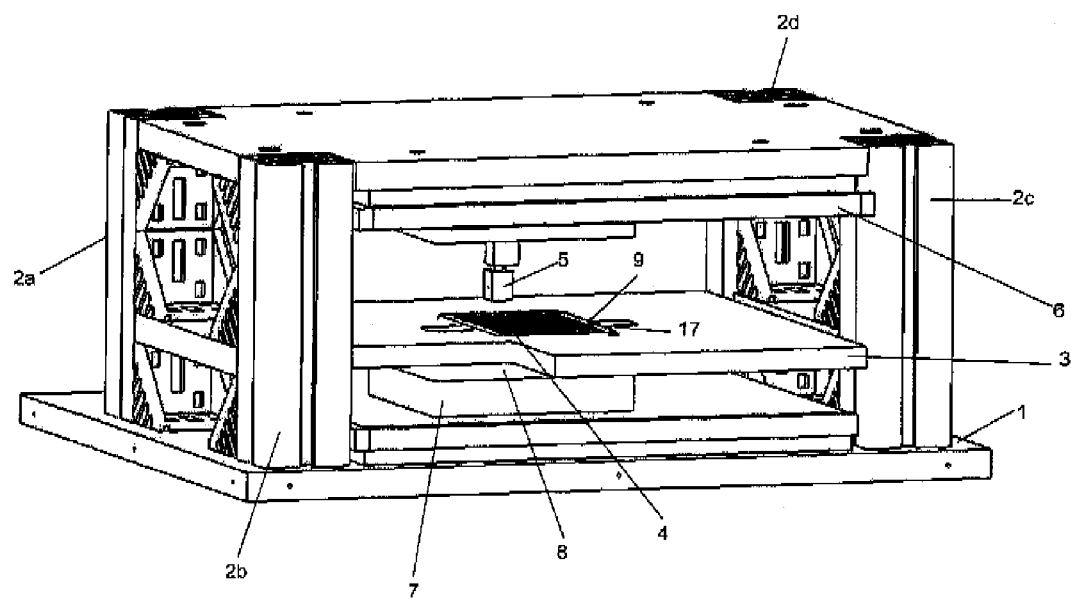

Figur 2
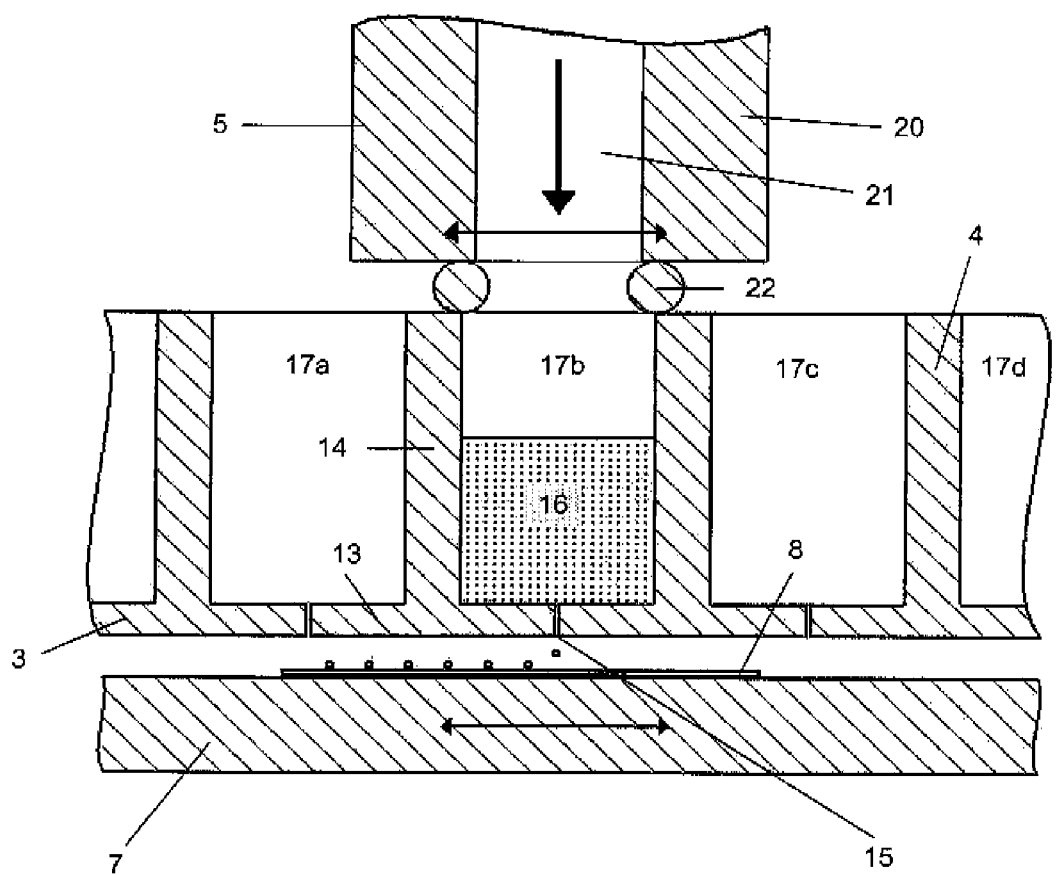

DEVICE FOR RECEIVING A LIQUID AND ALSO DEVICE FOR APPLYING LIQUIDS ON SAMPLE CARRIERS AND METHOD FOR THIS PURPOSE

CROSS REFERENCE TO RELATED APPLICATIONS

This application claims the benefit of U.S. Provisional Patent Application No. 61/110,027, filed Oct. 31, 2008, the entire disclosure of which is hereby incorporated by reference.

BACKGROUND

The present invention relates to a device for receiving liquids and also to a device for applying liquids on sample carriers and to a corresponding method for this purpose.

The trend in biotechnology leads to the processing of increasingly smaller quantities of liquid. The reasons for this are very varied. Often the substances to be examined are very expensive since usually in fact a large number of steps is required for the production thereof. In part they concern biologically dangerous materials, the handling of which in very small quantities can reduce the risk enormously. However frequently also only very small quantities of the sample volume are available but, at the same time, as many tests as possible are intended to be implemented. Also the speed of the reactions depends significantly upon the sample volume. The smaller this is, the faster the analysis. Modern diagnosis apparatus is able to analyse thousands of adjacently printed spots at the same time on one microarray.

Over the years, specific standards in tests have been established. Thus frequently disposable articles made of injection-moulded polypropylene or polystyrene are used since the very costly cleaning and disinfection of the sample containers is thus dispensed with. These microtitre plates can be found in various designs. They differ mainly in the number of sample volumes. Thus there are 96-, 384- but also 1536-well plates which in fact have the same outer dimensions but differ in the volume and number of wells.

The difficulty resides in placing the reagents from the wells on the microarray. Simple metering methods with pipettes and by hand are very time-consuming and imprecise. In order to avoid cross-contaminations, the pipette tip must be exchanged after each sampling. This is also the reason why piezo dispensers which firstly remove the liquid and then place it on the microarray are not possible.

Previous approaches to the solution are restricted either to a completely new configuration of the sample container (MTP) or the volume is placed on the sample carrier via an intermediate station, i.e. not directly.

In the case of the "TopSpot-Method", a print head made of silicon and glass is manufactured and a series of microchannels conducts the liquids then into the specially produced nozzles. A pressure pulse is produced via a plunger and places the drop at the outlet of the nozzle. The disadvantage of this method resides in the fact that, for each new printing process, the print head must firstly be disinfected and cleaned in order to preclude cross-contamination. In addition, the production of these print heads is relatively complex and expensive. A further disadvantage of the method resides in the fact that the printed grid always has a fixed spot spacing of for example 500 μm. The wells can only all be printed at the same time and in a fixed position. Before printing can take place with this method, the print head must firstly be filled since printing cannot take place directly from the reaction vessel. The dead volume is high due to the long channels.

The "Dispensing Wellplate (DWP) method" functions similarly. The metering volume here is however not controlled via the pulse duration or the stroke but the entire micronozzle which has a strictly defined volume is emptied.

A third variant is the removal of the desired quantity of liquid via "pipettes" which then "deposit" this on the sample carrier. The great disadvantage in this variant is contamination of the pipette. After each printing process, said pipette must be cleaned, which results inter alia in the fact that a part of the liquid is always lost. The danger of cross-contaminations with this method is very high.

SUMMARY OF THE INVENTION

It is hence the object of the present invention to provide a device by means of which small, variable volumes of liquid which can be produced independently of each other can be applied individually or simultaneously without cross-contamination directly on sample carriers or on freely choosable positions on sample carriers.

This object is achieved by a device according to claims 1 and 12 and by a method according to claim 10. Advantageous developments of the devices according to the invention and also of the method according to the invention are provided in the respective dependent claims.

According to the invention, the bases of the depressions of the device according to the claim for receiving and dispensing liquids have very small borings so that the capillary pressure in the boring is greater than the pressure due to the liquid level. Hence leakage is prevented. Via a pulse, such as for example a pneumatic pressure pulse, a sample, the volume of which is controlled via the number of drops and the pulse duration, can be removed.

In theory, the principle can be represented as follows:

The capillary pressure ($P_{cap}$) of a thin boring is calculated by $$P_{cap} = \frac{2 \cdot \sigma \cdot \cos\Theta}{r}$$

$P_{cap}$: Capillary pressure
σ: Surface tension of the liquid
Θ: Wetting angle
r: Hole radius The capillary pressure acts counter to the pressure which is produced in the well by the liquid level ($P_{well}$). This is calculated by:

$$P_{well} = \rho \cdot h \cdot g$$

$P_{well}$: Pressure acting at the bottom of the liquid column
ρ: Density of the liquid
g: Acceleration due to gravity
h: Height of the liquid column Hence, for example in the case of a 96-well microtitre plate made of polypropylene with a wetting angle of 82° by water, the result is a theoretical boundary filling level of 41 mm, from which the capillary pressure no longer suffices in a circular boring with 50 μm radius to keep the well sealed at the bottom. Because of a maximum possible filling level of 10.9 mm in a 96-well plate, no sealing problems consequently occur.

According to the invention, there should be understood by the term "boring" a through-opening from the inside of the base of a depression up to the underside of the base of a depression. The borings have a diameter of 1-400 µm, 25-100 µm, preferably of less than or equal to 50 µm. Furthermore, the borings can have for example a length of 50-2000, 1000-1300, 150-250, preferably of 1200 µm and/or 200 µm.

According to the invention, there should be understood by the term "compressed air plunger", a compressed air supply device which has a cavity at the end thereof surrounded by a wall, the wall of the compressed air plunger forming a seal with the wall of a depression according to the claim or of a well in order to produce a corresponding excess pressure in the respective depression or well.

The fact that the reactions to be examined (for example cell growth, cleaning or the like) can take place directly in device according to the claim, such as e.g. a multiwell plate from which printing can also take place subsequently, represents an advantage of the present invention. Because processing and handling of the samples from one vessel into a new one is dispensed with, dangers of contamination of the sample are hence minimised. The lack of danger of cross-contamination represents a further advantage since the dispensing of the different liquids/reagents is effected in parallel and/or can be implemented individually directly from each depression.

According to the invention, preferably standardised multiwell plates are used as devices for receiving liquids since these are compatible with most filling and processing systems. The principle according to the invention can be applied to all MTP formats.

The multiwell plates according to the invention can comprise any material which is suitable for the production of a multiwell plate, such as e.g. any injection-moulded or mouldable polymer. Preferably, they comprise polypropylene or polystyrene. Furthermore, the multiwell plates according to the invention can comprise for example 96, 384, 1536 wells without being restricted hereto.

From the multiwell plates according to the invention, for example metering volumes of 0.1 nanoliters can be taken (dependent upon the hole diameter and upon the sample properties). However the complete wells or one or more wells can also be emptied completely at the same time via a continuous pulse or many individual pulses. All desired metering volumes in between can be adjusted in any way. Dead volumes are not present since the multiwell plates can be printed until completely empty.

As a replacement for the borings according to the invention, thin capillaries (e.g. glass) can be used, said capillaries being introduced into the well base. Good results can be achieved herewith.

Furthermore, the use also of a thin glass plate as well base is possible. Very small borings can be placed in these. Furthermore, it is possible that the well bases of the multiwell plates are formed by a film, for example a plastic material film which is glued on the underside of the multiwell plate or laminated thereon, and are placed in the corresponding borings by means of for example a laser.

Use of this technique in vessels other than normal multi-well plates is also possible.

Other aspects, features, and advantages of the present invention will be apparent to one skilled in the art from the description herein taken in conjunction with the accompanying drawings.

BRIEF DESCRIPTION OF THE DRAWINGS

Further subjects of the present invention are a device for applying quantities of liquids on sample carriers and also a method for this purpose, the principle of which is described subsequently with reference to FIGS. 1 and 2 and a preferred embodiment, without being restricted hereto. There are shown in:

FIG. 1 a device according to the invention for applying liquids on sample carriers and FIG. 2 a section from a device according to the invention according to FIG. 1.

DETAILED DESCRIPTION OF THE PRESENT INVENTION

FIG. 1 shows a device according to the invention for applying liquids on a sample carrier. This device has a base plate 1 on which four supports 2*a*, 2*b*, 2*c* and 2*d* are disposed as holders for the further elements of the device. There are disposed on the four supports in vertical sequence upwards a sample holder 8 which is disposed on a moving mechanism 7 for horizontal movement of the sample holder 8 in the two horizontal Cartesian coordinates. Above this sample holder, a holder 3 which has an opening 9 in the form of a microtitre plate is disposed on the supports 2*a* to 2*d*. In this opening 9, a microtitre plate 4 which has for example 96 cups (wells) 17 in a rectangular arrangement is disposed. As a result of the arrangement of the microtitre plate 4 in the opening 9, the base of the microtitre plate is situated accessible for the most part above the sample receiving means 8.

Above the holder 3 and the microtitre plate 4, a moving mechanism 6 is disposed, on the underside of which a print head or element for producing an (air) pressure 5 is disposed. With the moving mechanism 6, the print head 5 (compressed air plunger) can be moved both in the horizontal in all directions and in the vertical.

FIG. 2 now explains the method according to the invention further.

As can be detected, the print head 5 has a wall 20 and an interior space 21, a specific air pressure being able to be produced in the interior space.

The microtitre plate 4 has a sequence of cups (wells) 17*a* to 17*d* which are separated from each other by walls 14. On the underside thereof, these cups have a base 13, a boring 15 being provided in the wall 14, in the centre in the base 13 with respect to each individual cup 17*a* to 17*d*, said boring passing from the interior space 16 of the cups through the wall 14 and allowing passage of liquid from the interior space 16 outwards. The boring is thereby dimensioned such that the capillary pressure in the boring is greater than the hydrostatic pressure of the liquid situated in the cup 17*b*.

The walls of the print head 5 and of the individual cups 17*a* to 17*d* have the same geometric shape and the same dimensioning in cross-section so that they can be disposed one above the other to form a seal. In order to improve the seal, a sealing ring 22 is situated on the underside of the wall 20 of the print head 5, said sealing ring coming to be situated between the wall 20 of the print head 5 and the wall 14 of the cup 17*b* represented in FIG. 2 and sealing these two walls. In order now to meter out a liquid from the volume 16 of the cup 17*b* via the capillary boring 15, an increased pressure is exerted via the print head 5 on the liquid in the cup 17*b*, said pressure exceeding the capillary pressure of the boring 15. In this way, a drop from the cup 17*b* is metered to the sample receiving means 8.

The sample receiving means 8 can likewise be moved in all horizontal directions so that the place at which the liquid is metered on from the cup 17*b* can be chosen freely. In total, the result is that, with any choice of cup in the microtitre plate 4 and because of the ability of the of the print head 5 to approach the individual cups 17*a* to 17*d* and because of the individual displaceability of the sample receiving means 8 at any position of the sample receiving means, any liquid can be metered on from any cup 17a to 17d.

The same result can be achieved if the print head 5 and the microtitre plate 4 are moveable or the microtitre plate 4 and the sample receiving means 5 are moveable.

In the case where the number of print heads is chosen such that one print head is assigned to each well of the microtitre plate, it is sufficient merely to configure the sample holder to be moveable.

The function is described in detail subsequently with reference to FIG. 2.

The vertically moveable print head/plunger 1 is positioned relative to the multiwell plate 4 precisely horizontally via the first moving mechanism 6 and transmits a pressure pulse to the well 17b. The seal 22 ensures complete transmission of the pulse. The boring 15 in the well base 13 represents the only route which the liquid in the well 17b can take. Since the pressure pulse is very short, one drop is generated at the boring outlet and is deposited on the sample carrier 8 of the second moving mechanism 7 which is situated thereunder.

As a result of the fact that the plunger 5 can approach the desired positions (wells 17a to 17b) rapidly in succession and can produce there respectively the desired number of precisely defined sample volumes, any metering volumes can be taken from any number of wells.

In addition, the second moving mechanism 7 displaces the sample holder 8, coordinated precisely positionally and temporally, under the multiwell plate 4 such that the produced drops are deposited in the desired grid on the sample carrier 8.

Both the first and the second moving mechanism are displaceable horizontally and vertically relative to the multiwell plate 4.

In the present embodiment according to the invention, given by way of example, a plunger, in particular a compressed air plunger is used. Instead of one plunger, also a plurality of plungers or one plunger per well can however be used. Furthermore, instead of plungers, in particular compressed air plungers, also pistons which are configured on their contact faces with a multiwell plate in a seal can be used. On their contact face with the multiwell plate, the plungers or pistons can have for example a seal in the form of a sealing ring. It is however also possible to use an elastic cover instead of sealing rings, which cover has the corresponding openings above the wells and is applied on the upper side of the multiwell plate such that the openings are dimensioned such that the wall of the opening seals the compressed air plunger or piston relative to the well. In particular, the openings of the elastic cover can be dimensioned such that their maximum cross-section is less than or equal to the cross-section of a well. Instead of plungers or pistons, the multiwell plate can also be sealed at the top with a flexible membrane, by means of which a pressure pulse exerted on the membrane is transmitted to the wells.

The method according to the invention is extremely rapid since a printing process requires only a few milliseconds, according to the volume to be printed, and the moving mechanisms permit very high speeds.

The pressure pulse of the method according to the invention is achieved via a quick-acting valve in that the latter is opened for a short time. The quick-acting valve enables for example a pulse duration of approx. 0.5 ms.

Furthermore, the pressure pulse can also be achieved via the mechanical movement of a piezoactuator.

In general, filtered laboratory compressed air is used in conjunction with a quick-acting valve in order to produce the required pressure pulse. The use of other gases instead of air for applying the pressure pulse is however likewise possible. There should be mentioned here in particular gases which have lower compressibility than air since, when using such gases, effects caused by gas compression are minimised. Also the use of protective gases (e.g. noble gases) as process gas is possible. In this case, chemical reactions or other interactions between the liquid in the well and the process gas can be precluded.

Since printing can take place with the method according to the invention directly from a merely slightly modified multiwell plate, this method is extremely economical. The production costs of a corresponding multiwell plate, in the case of a suitable injection moulding tool and a sufficiently high piece number, are in the "cent range".

As a result, the multiwell plate according to the invention can be used as a disposable product. Therefore, no cleaning steps are required after the printing process since simply a new multiwell plate can be used.

Cross-contamination can be precluded since the plunger does not come into contact with the liquid in the well. In the case of applications with higher requirements, an individual plunger can even be used for each well since these can be constructed very economically. Furthermore, it is also possible to seal the microtitre plate at the top by means of a flexible membrane which transmits the pressure pulse.

Any combinations and patterns can be printed on the sample carrier since, with this system, there is no restriction to a fixed pattern in the array and mixtures can also be produced on the sample carrier. Furthermore, also a second multiwell plate can be used as sample carrier into which then any mixtures, any volumes can be printed. These can be printed subsequently on a suitable sample carrier for analysis with the same system.

There can be used in addition as sample carrier, for example glass slides (object carriers), biochips, microtitre plates or microarrays. There is termed biochip or microarray a carrier material on which a large number of biological or biochemical detections or tests can be carried out in the smallest, generally only fingernail-size space. The printing of object carriers for the production of biochips presents a huge challenge in the handling of the smallest quantities of liquid and of biologically active substances. The aim hereby is to parallelise the production of biochips as far as possible. For this purpose, the parallel cultivation of microorganisms, in multiwell plates of different sizes is already standard nowadays.

The method according to the invention can be used in many ways as "liquid handling" method, such as e.g.:

For printing all types of biochips and microarrays (protein microarray, DNA microarrays)

For reformatting samples in different plate formats.

As a quick method for increasing the throughput in high-throughput-screening (HTS) for example for selecting new cell strains in white biotechnology.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. An apparatus for applying liquids on sample carriers, comprising:
a holder for a device for receiving a liquid and from which the liquid is dispensed, the device comprising a plurality of depressions that are open at an upper end, wherein respective bases opposite the upper end of at least one, several or all depressions have at least one boring, at least one of the borings being configured in such a manner that capillary pressure in the respective boring is greater than a pressure which can be produced by the liquid in the respective depression;

a mechanism for producing a gas pressure pulse disposed above the holder for the device and in fluid communication with the respective upper end of at least one or several but not all of the depressions to receive the gas pressure pulse;

a holder for at least one sample carrier disposed below the holder for the device;

a plurality of support elements operating to support the holder for the device, the mechanism for producing a gas pressure pulse, and the holder for the at least one sample carrier; and at least one moving mechanism for moving the holder for the device relative to the plurality of support elements, such that the mechanism for producing a gas pressure pulse may be displaced horizontally with respect to the individual depressions of the device, which are to be supplied with the gas pressure pulse, such that the depressions with which the mechanism for producing a gas pressure pulse are in fluid communication are adjustable.

2. The apparatus according to claim 1, wherein at least two of the holder for the device, the mechanism for producing a gas pressure pulse, and the holder for at least one sample carrier are displaceable independently of each other with respect to the plurality of support elements, at least one of horizontally and vertically by a moving mechanism.

3. The apparatus according to claim 1, wherein the holder for the device includes the device therein.

4. The apparatus according to claim 1, wherein the mechanism for producing a gas pressure pulse is displaceable horizontally with respect to the plurality of support elements by a moving mechanism in such a manner that at least one, several or all of the depressions are simultaneously supplied with a gas pressure pulse by the mechanism for producing a gas pressure pulse.

5. The apparatus of claim 1, wherein the holder for at least one sample carrier is displaceable horizontally with respect to the plurality of support elements by a moving mechanism in such a manner that any sample carriers and/or positions on the respective sample carrier are approachable.

6. The apparatus according to claim 1, wherein the mechanism for producing a gas pressure pulse comprises at least one plunger and/or piston.

7. The apparatus according claim 6, wherein the plunger includes a contact face that contacts the device, and the contact face includes a seal in the form of a sealing ring and/or a sealing disc.

8. The apparatus according to claim 6, wherein the plunger is a pneumatically driven plunger.

9. The apparatus according claim 1, wherein the sample carrier is at least one of: a glass slide (object carrier), a biochip, a microtiter plate, a microarray, and the device.

10. A method for applying liquids on sample carriers, comprising:

simultaneously supplying depressions of a device with a pressure pulse by a mechanism for producing a pressure pulse, wherein:

the device includes a holder for receiving a liquid and from which the liquid is dispensed, the device comprising the depressions that are open at an upper end, wherein respective bases opposite the upper end of at least one, several or all of the depressions have at least one boring, at least one of the borings being configured in such a manner that capillary pressure in the respective boring is greater than a pressure which can be produced by the liquid in the respective depression;

the mechanism for producing a gas pressure pulse is disposed above the holder for the device and in fluid communication with the respective upper end of at least one or several but not all of the depressions to receive the gas pressure pulse;

a holder for at least one sample carrier is disposed below the holder for the device;

a plurality of support elements support the holder for the device, the mechanism for producing a gas pressure pulse, and the holder for the at least one sample carrier; and at least one moving mechanism moves the holder for the device relative to the plurality of support elements, such that the mechanism for producing a gas pressure pulse may be displaced horizontally with respect to the individual depressions of the device, which are to be supplied with the gas pressure pulse, such that the depressions with which the mechanism for producing a gas pressure pulse are in fluid communication are adjustable.

11. The method according to claim 10, further comprising controlling a volume of the liquid applied on the sample carrier by means of at least one of: the pressure pulse, a length of the pressure pulse, and a number of pressure pulses.

12. The method according to claim 10, further comprising: producing the pressure pulse by means of a quick-acting valve or a mechanical movement of a piezoactuator.

13. The method according claim 10, further comprising: producing the pressure pulse by means of air or a piston movement.

* * * * *